United States Patent
Torii et al.

(10) Patent No.: US 10,285,581 B2
(45) Date of Patent: May 14, 2019

(54) OPHTHALMOLOGIC INFORMATION PROCESSING APPARATUS AND OPHTHALMOLOGIC INFORMATION PROCESSING METHOD

(71) Applicant: NIDEK CO., LTD., Gamagori, Aichi (JP)

(72) Inventors: Hisanari Torii, Gamagori (JP); Norimasa Satake, Aichi (JP)

(73) Assignee: NIDEK CO., LTD., Gamagori, Aichi (JP)

(*) Notice: Subject to any disclaimer, the term of this patent is extended or adjusted under 35 U.S.C. 154(b) by 126 days.

(21) Appl. No.: 15/366,400

(22) Filed: Dec. 1, 2016

(65) Prior Publication Data
US 2017/0172405 A1 Jun. 22, 2017

(30) Foreign Application Priority Data
Dec. 2, 2015 (JP) .................. 2015-236160

(51) Int. Cl.
*G06K 9/00* (2006.01)
*A61B 3/00* (2006.01)
(Continued)

(52) U.S. Cl.
CPC .......... *A61B 3/0025* (2013.01); *A61B 3/0058* (2013.01); *A61B 3/102* (2013.01); *A61B 3/1005* (2013.01); *A61B 3/1225* (2013.01); *A61B 5/0066* (2013.01); *A61B 5/1072* (2013.01); *A61B 5/4842* (2013.01); *G06K 9/0061* (2013.01); *G06K 9/00201* (2013.01); *G06K 9/2018* (2013.01); *G06K 9/52* (2013.01);
(Continued)

(58) Field of Classification Search
CPC ..... A61B 3/0025; A61B 3/102; A61B 3/1005; A61B 3/1225; A61B 5/0066; G06T 2207/30041
USPC .......................................... 382/131
See application file for complete search history.

(56) References Cited

U.S. PATENT DOCUMENTS

| 2010/0194757 A1* | 8/2010 | Tonnidokoro | A61B 3/102 345/440 |
| 2012/0281184 A1* | 11/2012 | Torii | A61B 3/0025 351/206 |

(Continued)

FOREIGN PATENT DOCUMENTS

JP 2012-232034 A 11/2012

*Primary Examiner* — Van D Huynh
(74) *Attorney, Agent, or Firm* — Sughrue Mion, PLLC

(57) ABSTRACT

An ophthalmologic information processing apparatus for performing follow-up of a subject eye based on plural pieces of OCT data obtained at different dates includes: a processor; and memory storing computer readable instructions, when executed by the processor, causing the ophthalmologic information processing apparatus to execute: a first acquisition process of acquiring plural pieces of layer thickness information regarding a fundus, the plural pieces of layer thickness information being a processing result of the plural pieces of OCT data of the subject eye; a matching process of matching the pieces of layer thickness information based on the plural pieces of OCT data to each other in consideration of a difference in acquisition condition among the pieces of OCT data; and a display control process of displaying results of the matching of the pieces of layer thickness information on a monitor.

12 Claims, 3 Drawing Sheets

(51) Int. Cl.
  *G06T 7/50* (2017.01)
  *A61B 3/10* (2006.01)
  *A61B 3/12* (2006.01)
  *A61B 5/00* (2006.01)
  *G06K 9/52* (2006.01)
  *G06K 9/62* (2006.01)
  *G06T 7/00* (2017.01)
  *A61B 5/107* (2006.01)
  *G06K 9/20* (2006.01)

(52) U.S. Cl.
  CPC .......... *G06K 9/6215* (2013.01); *G06T 7/0012* (2013.01); *G06T 7/0016* (2013.01); *G06T 7/50* (2017.01); *A61B 5/7282* (2013.01); *G06T 2200/24* (2013.01); *G06T 2207/10101* (2013.01); *G06T 2207/30041* (2013.01)

(56) References Cited

U.S. PATENT DOCUMENTS

| | | | | |
|---|---|---|---|---|
| 2014/0112562 A1* | 4/2014 | Yamakawa | ............ | A61B 3/102 382/131 |
| 2015/0374228 A1* | 12/2015 | Satake | ................. | G06T 7/0016 351/206 |
| 2016/0302664 A1* | 10/2016 | Yamakawa | ........... | A61B 3/1005 |
| 2016/0317027 A1* | 11/2016 | Goto | ....................... | A61B 3/102 |
| 2016/0331224 A1* | 11/2016 | Uji | ....................... | A61B 3/0025 |

\* cited by examiner

OPHTHALMOLOGIC INFORMATION PROCESSING APPARATUS AND OPHTHALMOLOGIC INFORMATION PROCESSING METHOD

CROSS REFERENCE TO RELATED APPLICATION

This application is based upon and claims the benefit of priority of Japanese Patent Application No. 2015-236160 filed on Dec. 2, 2015, the contents of which are incorporated herein by reference in its entirety.

BACKGROUND

The present disclosure relates to an ophthalmologic information processing apparatus and an ophthalmologic information processing method for performing the follow-up of a subject eye based on plural pieces of OCT data obtained at different dates and times.

BACKGROUND ART

Pieces of OCT data regarding a subject eye may be acquired at different dates and times by an ophthalmologic apparatus such as optical coherence tomography (OCT) for ophthalmology to thereby perform the follow-up of the subject eye. For example, OCT data regarding the fundus is acquired a plurality of times, and the course of a lesion portion is observed from changes in the OCT data.

RELATED ART DOCUMENT

Patent Document

[Patent Document 1] JP-A-2012-232034

SUMMARY OF THE INVENTION

Problem that the Invention is to Solve

In an ophthalmologic field, it is necessary to perform follow-up over several years in a case of, for example, glaucoma, and the follow-up may performed over several tens of years in a longer case. When a plurality of years elapses, an apparatus used for the acquisition of OCT data may be changed to an apparatus having different specifications. In addition, even when an apparatus having the same specifications is used, an acquisition condition other than the specifications of the apparatus may vary depending on a time when data is acquired. In a case where plural pieces of OCT data acquired under different acquisition conditions are used, it is considered that it is difficult to satisfactorily perform follow-up.

SUMMARY

An object of this disclosure is to provide an ophthalmologic information processing apparatus capable of satisfactorily performing the follow-up of a subject eye, and an ophthalmologic information processing method.

An aspect of the present disclosure provides the following arrangements:

An ophthalmologic information processing apparatus for performing follow-up of a subject eye based on plural pieces of OCT data obtained at different dates, the ophthalmologic information processing apparatus comprising:

a processor; and memory storing computer readable instructions, when executed by the processor, causing the ophthalmologic information processing apparatus to execute:

a first acquisition process of acquiring plural pieces of layer thickness information regarding a fundus, the plural pieces of layer thickness information being a processing result of the plural pieces of OCT data of the subject eye;

a matching process of matching the pieces of layer thickness information based on the plural pieces of OCT data to each other in consideration of a difference in acquisition condition among the pieces of OCT data; and a display control process of displaying results of the matching of the pieces of layer thickness information, which is performed by the matching process, on a monitor.

An ophthalmologic information processing method for performing follow-up of a subject eye based on plural pieces of OCT data obtained at different dates and times, the ophthalmologic information processing method comprising:

a first acquisition process of acquiring plural pieces of layer thickness information regarding a fundus, the plural pieces of layer thickness information being a processing result of the plural pieces of OCT data of the subject eye;

a matching process of matching the pieces of layer thickness information based on the plural pieces of OCT data to each other in consideration of a difference in acquisition condition among the pieces of OCT data; and a display control process of displaying results of the matching of the pieces of layer thickness information, which is performed by the matching process, on a monitor.

BRIEF DESCRIPTION OF THE DRAWINGS

FIG. 4 is a diagram quoted from "Progress of optical coherence tomography for fundus, Medical Photonics No. 7", Optronics Co., Ltd., issued on November 2011".

DESCRIPTION OF ILLUSTRATIVE EMBODIMENTS

Figure 1:
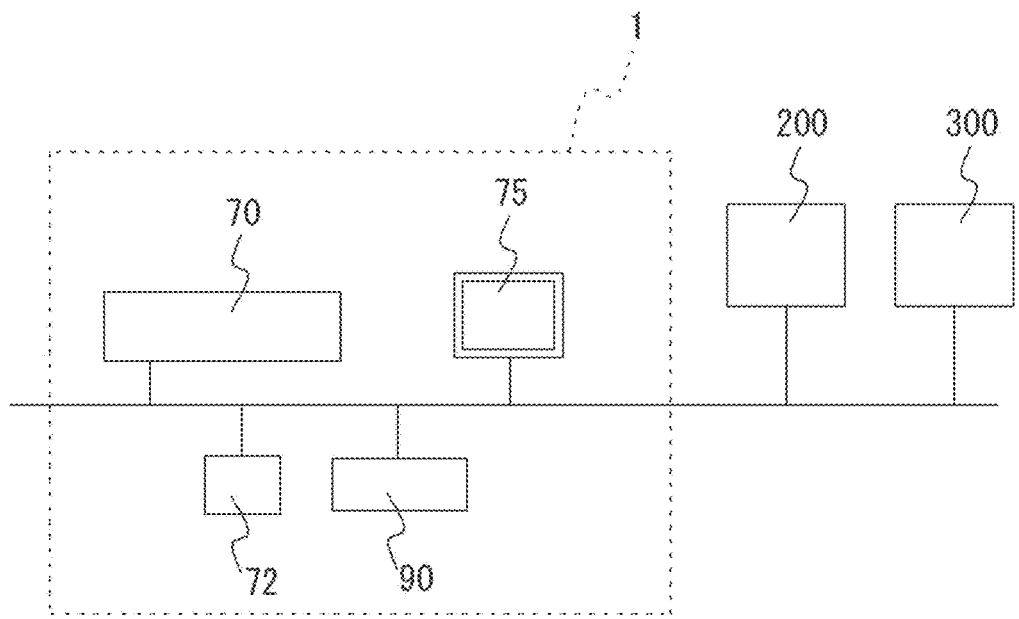
FIG. 1 is a block diagram illustrating a configuration of an ophthalmologic information processing apparatus according to this embodiment.

A typical embodiment according to this disclosure will be described with reference to the accompanying drawings. FIG. 1 is a block diagram illustrating a schematic configuration of an ophthalmologic information processing apparatus 1 of this example. In the following embodiment, the ophthalmologic information processing apparatus 1 is used to perform the follow-up of a subject eye based on plural pieces of OCT data (in other words, time-series OCT data) which are acquired at different dates and times over a long period of time. In the following description, the ophthalmologic information processing apparatus 1 is simply referred to as "this apparatus 1". The ophthalmologic information processing apparatus may be a computer which is embedded in an imaging apparatus for ophthalmology, or may be a computer which is separate from an imaging apparatus.

This apparatus 1 illustrated in the example of FIG. 1 mainly includes a control unit 70 and a memory (storage unit) 72. In addition, this apparatus 1 may include an operation unit (input interface) 90 and a monitor 75.

The control unit 70 is a processing apparatus (processor) that includes an electronic circuit performing a control process of each unit and a computational process. The control unit 70 is realized by a central processing unit (CPU), a memory, and the like. The control unit 70 is used as, for example, a display control unit and an image processing unit.

In addition, this apparatus 1 may be connected to a first imaging apparatus 200 and a second imaging apparatus 300, as illustrated in FIG. 1. The apparatuses may be connected to each other through a network (a bus, a LAN, or the like), and can transmit and receive image data and the like to and from each other. Meanwhile, this apparatus 1 does not need to be connected to the imaging apparatus 200 and the imaging apparatus 300 at the same time. In long-term follow-up, a certain imaging apparatus connected to this apparatus 1 may be changed to another imaging apparatus.

The imaging apparatuses 200 and 300 are OCT devices that include a tomographic imaging optical system (for example, optical coherence tomography (OCT)). The imaging apparatuses 200 and 300 divide light flux emitted from a light source into measurement light and reference light, and guide the measurement light to the fundus of a subject eye. In addition, interference signals of the reference light and return light of the measurement light from the fundus are acquired by a detector. As a result, OCT data is acquired (generated) based on the interference signals obtained by the detector. Meanwhile, it is assumed that image processing units generating the OCT data based on the interference signals are respectively provided in the imaging apparatuses 200 and 300 as bodies separate from this apparatus 1, for example, in this embodiment. However, this disclosure is not limited thereto, and this apparatus 1 may also serve as a processor (for example, an image processing unit) of each of the imaging apparatuses 200 and 300. Meanwhile, the OCT data acquired by the imaging apparatuses 200 and 300 may be, for example, either one-dimensional OCT data or three-dimensional OCT data.

Figure 2:
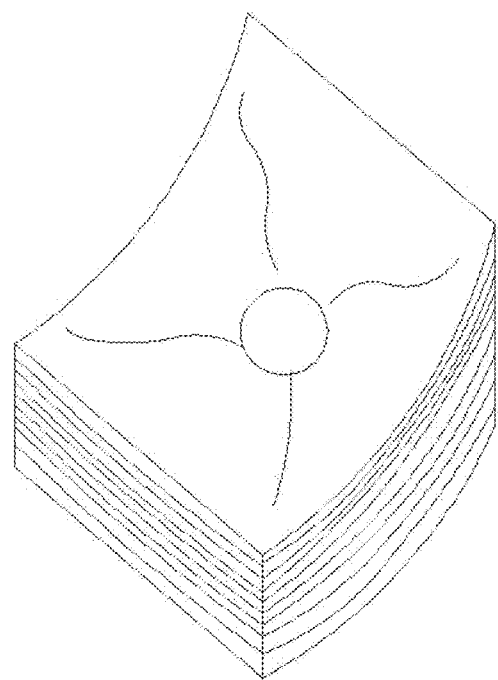
FIG. 2 is a diagram illustrating three-dimensional image data which is an example of OCT data.

Here, the one-dimensional OCT data may be a reflection intensity distribution (that is, A scan (depth profile)) in the depth direction at one point on the fundus, or may be one-dimensional function OCT data (motion contrast data or the like, as an example of functional OCT data) at the point. The two-dimensional OCT data is data obtained by one-dimensionally performing scanning with measurement light on the fundus. The two-dimensional OCT data may be a two-dimensional reflection intensity distribution (for example, a tomographic image) in a certain tomographic plane, or may be function OCT data in the tomographic plane. The three-dimensional OCT data is, for example, data obtained by two-dimensionally performing scanning with measurement light on the fundus. The three-dimensional OCT data may be a three-dimensional image (see FIG. 2) showing the structure of the fundus, or may be three-dimensional function OCT data.

The imaging apparatus 200 and the imaging apparatus 300 may be OCT devices having different specifications (mainly, specifications of an optical system). For example, imaging methods of the imaging apparatus 200 and the imaging apparatus 300 may be different from each other. As an example, in the following description, it is assumed that the imaging apparatus 200 is SD-OCT (spectral domain OCT) and the imaging apparatus 300 is SS-OCT (swept source OCT). In this case, the imaging apparatus 200 includes a light source that emits light flux having a small coherent length, as a light source, and includes a spectroscopic detector that detects interference signals of reference light and return light of measurement light from a subject eye for each wavelength component, as a detector. The imaging apparatus 200 obtains OCT data of a subject eye based on an interference signal in each wavelength which is obtained by the spectroscopic detector. On the other hand, the imaging apparatus 300 includes a wavelength sweeping light source that temporally sweeps an emission wavelength, as a light source, and includes a point detector as a detector. The point detector may be one detector, or may be a balance detector that performs balance detection by using a plurality of (for example, two) detectors. The imaging apparatus 300 samples interference signals of reference light and return light of measurement light in accordance with changes in emission wavelength by a wavelength sweeping light source, and obtains OCT data of a subject eye based on an interference signal in each wavelength which is obtained by sampling. However, an imaging method of each apparatus is not limited thereto.

Pieces of OCT data obtained by the imaging apparatuses 200 and 300 are transmitted to this apparatus 1 through a network. This apparatus 1 acquires pieces of OCT data acquired by, for example, the imaging apparatuses 200 and 300 through a network, stores the pieces of OCT data (for example, three-dimensional tomographic image data (see FIG. 2), front image data, and the like) in the memory 72, and manages the stored pieces of OCT data. In addition, this apparatus 1 analyzes the acquired OCT data and outputs analysis results (for example, displays the analysis results on the monitor 75).

For example, the control unit 70 processes the pieces of OCT data (herein, three-dimensional OCT data) of the subject eye which are acquired by the imaging apparatuses 200 and 300 to acquire layer thickness information of the fundus. Here, the layer thickness information is information regarding the thickness of a layer constituting the fundus. Examples of the layer thickness information include information regarding the thickness of the entire fundus, information regarding a thickness for each of portions such as the retina, the choroid, and the sclera, information regarding the thickness of a layer constituting each of the portions, and the like. Meanwhile, in a case where a layer thickness is obtained, for example, the division processing of OCT data is performed for each layer by performing imaging processing (for example, a segmentation process) on the OCT data, and thus the thickness of each layer is measured based on an interval at a layer boundary.

Hereinafter, a case where at least retina thickness information which is information regarding the thickness of the retina is acquired by the control unit 70 will be described as a specific example. As the retina thickness, for example, thicknesses of respective layers of the retina (specifically, the thickness of an optic nerve fiber layer (NFL), the thickness from an internal limiting membrane (ILM) to a retinal pigment epithelium (RPE), and the like) may be acquired. The control unit 70 generates two-dimensional retina thickness information (for example, a layer thickness map) by using retina thicknesses at respective locations on the fundus which are obtained from images that differ in a scanning position on the fundus.

In this embodiment, the follow-up of two-dimensional retina thickness information is performed using a layer thickness map. The layer thickness map acquired (or generated) by this apparatus 1 is stored in the memory 72 by the control unit 70. In addition, the control unit 70 may generate an analysis chart based on layer thickness information, and may store the analysis chart in the memory 72.

Meanwhile, the thickness of the choroid may be measured by processing an acquired tomographic image. Naturally, the follow-up of a two-dimensional choroid thickness information (thickness map) may be performed.

In the following description, for convenience of description, it is assumed that the control unit 70 acquires layer thickness information based on acquired pieces of OCT data whenever the pieces of OCT data are acquired from the imaging apparatuses 200 and 300, and is stored in the memory 72. Meanwhile, a timing at which layer thickness information is generated from the pieces of OCT data is not limited thereto. For example, the layer thickness information may be generated from the pieces of OCT data at a timing when the pieces of OCT data are compared with each other.

Here, the gradation, contrast, and S/N ratio of the OCT data, and the like which are acquired in the OCT device may vary by changes in acquisition conditions of the OCT data in the OCT device. As a result, it is considered that a difference in acquisition condition affects layer thickness information which is acquired as a processing result of the OCT data. The wording "acquisition condition" as used herein includes, for example, at least a condition regarding specifications of the device in the OCT device that acquires the pieces of OCT data. As a specific example, conditions such as an acquisition method for OCT data (imaging method), a wavelength band of measurement light emitted from a measurement light source, light reception characteristics of a detector, and the resolution of OCT data are described.

As described above, in a case where OCT data is acquired a plurality of times over a long period of time for follow-up, acquisition conditions may be different from each other in the respective pieces of OCT data. In this case, pieces of layer thickness information obtained from the respective pieces of OCT data are not matched to each other, and thus it is considered that it is difficult to compare the pieces of layer thickness information with each other.

On the other hand, in this embodiment, the control unit 70 matches pieces of layer thickness information based on the respective pieces of OCT data to each other in consideration of a difference between acquisition conditions in the respective pieces of OCT data, and outputs matching results (matching process). In this matching process, the control unit 70 matches the pieces of layer thickness information to each other with respect to at least the depth direction. At the same time, the pieces of OCT data may be matched to each other with respect to the transverse direction (direction that intersects the depth direction). As a result of the matching process, an examiner can satisfactorily perform follow-up based on layer thickness information. Meanwhile, the matching process will be described later in detail.

The memory 72 is a rewritable nonvolatile storage medium. As the memory 72, for example, any of a hard disk, a flash memory, an external server, and a USB memory may be used.

Figure 3:
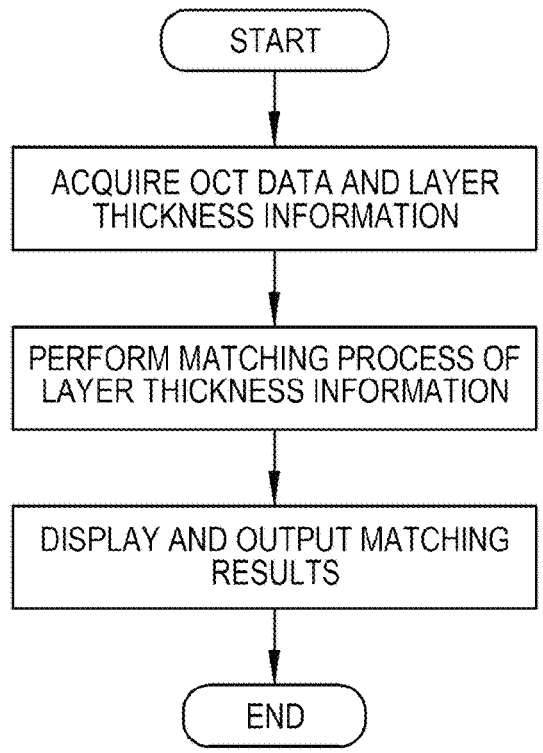
FIG. 3 is a flow chart illustrating an example of the operation of a control unit in the ophthalmologic information processing apparatus.

The memory 72 stores, for example, various programs for operating this apparatus 1. For example, an analysis program (ophthalmologic information processing program in this embodiment) which is stored in the memory 72 is processed (executed) by the control unit 70, and thus the operation of this apparatus 1 illustrated in the flow chart of FIG. 3 is executed.

The memory 72 stores, for example, pieces of OCT data acquired through the imaging apparatuses 200 and 300, layer thickness information obtained by processing the OCT data, and the like. Meanwhile, in the following description, layer thickness information based on OCT data obtained by the imaging apparatus 200 will be referred to as "first layer thickness information", and layer thickness information based on OCT data obtained by the imaging apparatus 300 will be referred to as "second layer thickness information".

Further, information for specifying an acquisition condition in OCT data (hereinafter, referred to as "acquisition condition data") may be stored in association with each of OCT data and layer thickness information. In this embodiment, acquisition condition data specifies at least specifications of an OCT device used for the acquisition of OCT data. Meanwhile, data for specifying specifications of a device may be, for example, at least any one of a model name of an OCT device, version information of the model, an imaging method of the OCT device, a wavelength band of measurement light emitted from a measurement light source, and light reception characteristics of a detector.

Such acquisition condition data may be data which is stored in a storage unit of each of the imaging apparatuses 200 and 300 and is transmitted to this apparatus 1 from each of the imaging apparatuses 200 and 300 together with OCT data. In this case, the control unit 70 of this apparatus 1 may store the OCT data and the acquisition condition data, which are received together, in the memory 72 in association with each other.

However, the acquisition condition data does not necessarily have to be data which is received by this apparatus 1 from the imaging apparatuses 200 and 300. For example, the acquisition condition data may be information which is manually input (or selected) by an examiner through an input interface 90. More specifically, after OCT data is stored in the memory 72, an examiner inputs (or selects) information corresponding to an acquisition condition of the OCT data through the input interface 90, and acquisition condition data corresponding to the OCT data may be acquired (for example, may be stored in the memory 72) as a result of the input (or selection). In addition, the OCT data, the layer thickness information, and the acquisition condition data are stored in association with a time axis, for example, for follow-up. The layer thickness information using a time as a function indicates changes in a layer thickness over time.

Further, the memory 72 may store a normal eye database in which layer thickness information in a normal eye is stored.

The input interface 90 receives the input of an examiner's operation. As the input interface 90, a device such as a mouse, a track ball, or a touch panel may be used.

The monitor 75 displays a graphic image obtained by visualizing OCT data (for example, a tomographic image or the like), layer thickness information, matching results of plural pieces of layer thickness information, and the like. The monitor 75 may be a touch panel. In this case, the monitor 75 functions as a portion of the input interface 90.

<Description of Operation>

Next, the operation of this apparatus 1 will be described more specifically with reference to the flow chart of FIG. 3.

For convenience of description, in the following description, the operation of this apparatus 1 will be described on the assumption that plural pieces of OCT data acquired over a long period of time are stored in the memory 72 in advance and are acquired as follows. Here, first, pieces of OCT data of a subject eye are acquired a plurality of times at different dates and times by the imaging apparatus 200 (SD-OCT). Then, pieces of OCT data of the subject eye are acquired a plurality of times at different dates and times by the imaging apparatus 300 (SS-OCT). In addition, pieces of OCT data are acquired by this apparatus 1 through a network whenever each of the imaging apparatuses 200 and 300 acquires OCT data, and thus plural pieces of OCT data acquired at different dates and times are stored in the memory 72. In other words, the memory 72 stores time-series OCT data in a subject eye.

In addition, for convenience of description, in the following description, it is assumed that layer thickness information (here, a layer thickness map) based on pieces of OCT data and acquisition condition data indicating acquisition conditions for the pieces of OCT data are stored in the memory 72 in association with each of the pieces of OCT data.

For example, in a case where the display (for example, a graphic image) for follow-up is output, the control unit 70 selects two or more pieces of layer thickness information used for follow-up among plural pieces of layer thickness information stored in the memory 72, and matches the selected pieces of layer thickness information to each other. The control unit 70 selects layer thickness information designated by an examiner through, for example, the input interface 90, as time-series layer thickness information used for follow-up. Data which is a standard for comparison in follow-up may further be selected among the selected pieces of layer thickness information.

In this operational example, one or more pieces of first layer thickness information based on OCT data obtained by the imaging apparatus 200 (SD-OCT) and one or more pieces of second layer thickness information based on OCT data obtained by the imaging apparatus 300 (SS-OCT) may be selected as time-series layer thickness information used for follow-up.

Figure 4:
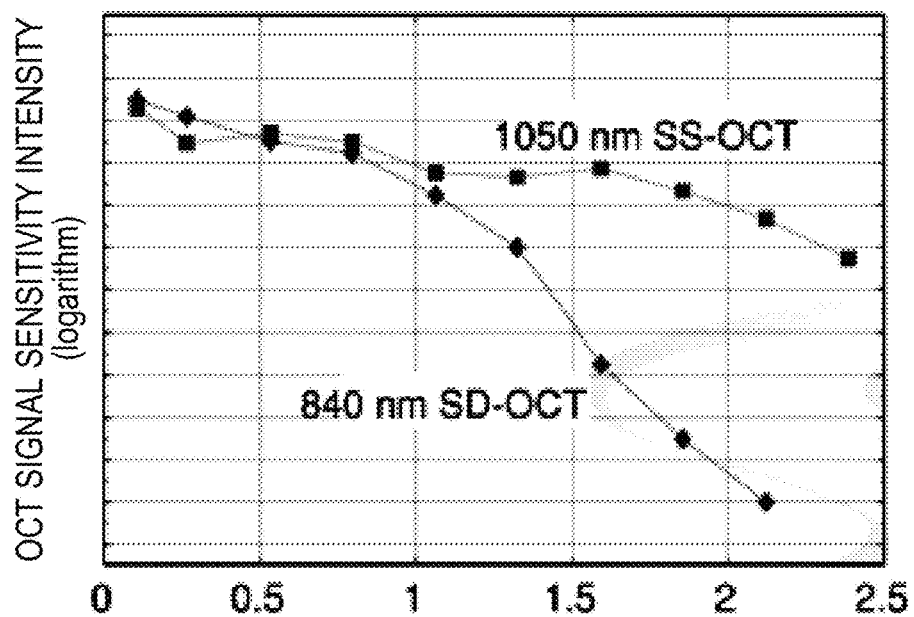
FIG. 4 is a graph illustrating a relationship between SD-OCT, a depth in SS-OCT, and OCT signal sensitivity intensity. Meanwhile.
Figure 5:
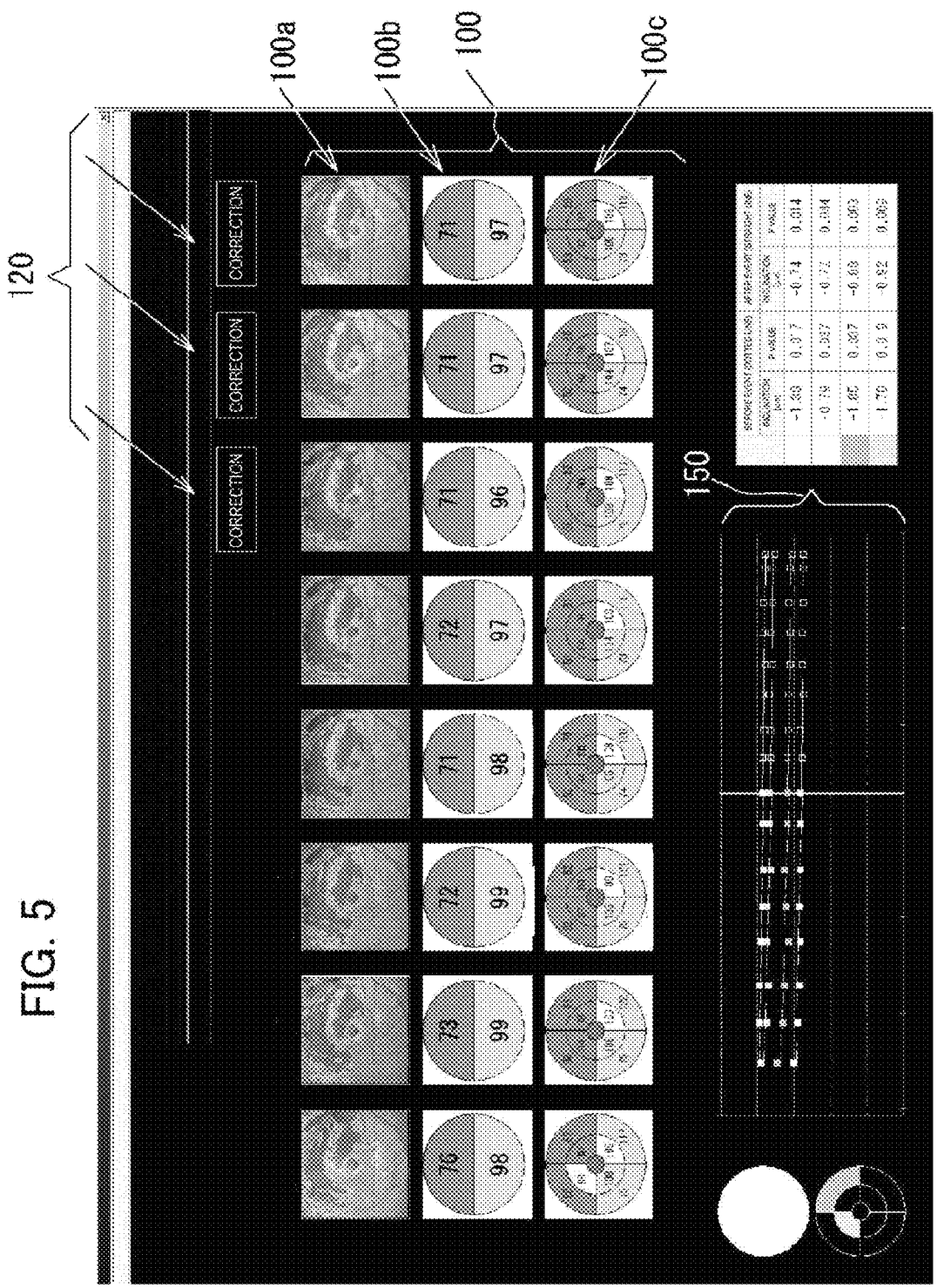
FIG. 5 illustrates an example of display output of plural pieces of layer thickness information matched by the control unit.

Here, in an ophthalmologic field, there is a tendency for a light source of SD-OCT having a central wavelength of 800 nm to 900 nm to be used as a light source of measurement light of OCT data. On the other hand, there is a tendency for a light source performing wavelength sweeping (performing wavelength sweeping centering around approximately 1050 nm) in a so-called 1-μm band to be used as a light source of SS-OCT. There is a tendency for a reaching depth of a measurement light and sensitivity in a deep portion (for example, the outer layer side of the retina) in SS-OCT to be higher than those in SD-OCT due to such a difference in a wavelength region of measurement light (see FIG. 4). On the other hand, with respect to sensitivity in a shallow portion (for example, the inner layer side of the retina), a significant difference is not seen at present, as compared to the deep portion. For this reason, in the first layer thickness information based on OCT data obtained by SD-OCT (imaging apparatus 200), at least the value of a layer thickness on the deep portion side may tend to become smaller than that in the second layer thickness information based on OCT data obtained by SS-OCT (imaging apparatus 300).

In addition, it is considered that OCT data acquired by the imaging apparatus 200 and OCT data acquired by the imaging apparatus 300 have different resolutions due to a difference in specifications of the OCT device. For example, such a difference may be caused due to a difference in a bandwidth of measurement light (the width of a wavelength band used as measurement light) between the imaging apparatus 200 (SD-OCT) and the imaging apparatus 300 (SS-OCT), or the like. It is considered that such a difference in resolution also affects the first layer thickness information and the second layer thickness information in different ways.

In this manner, in this embodiment, it is considered that it is difficult to compare the first layer thickness information and the second layer thickness information with each other due to a difference in specifications between the imaging apparatus 200 and the imaging apparatus 300 which acquire OCT data. The specifications of the imaging apparatus 200 and the imaging apparatus 300 may be specified by acquisition condition data corresponding to the first layer thickness information and acquisition condition data corresponding to the second layer thickness information. Consequently, in this apparatus 1, correction data of layer thickness information due to a difference in specifications between the imaging apparatus 200 and the imaging apparatus 300 are acquired based on the acquisition condition data corresponding to the first layer thickness information and the acquisition condition data corresponding to the second layer thickness information. At least one of the first layer thickness information and the second layer thickness information is corrected based on the correction data, to thereby match the first layer thickness information and the second layer thickness information to each other with respect to at least the depth direction (matching process).

The term "matching" as used herein may refer to, for example, correction of the value of a layer thickness in at least one of the first layer thickness information and the second layer thickness information. In this case, for example, one of the first layer thickness information and the second layer thickness information may be corrected based on an acquisition condition of the other layer thickness information. In addition, both the first layer thickness information and the second layer thickness information may be corrected based on a predetermined acquisition condition different from both an acquisition condition in the first layer thickness information and an acquisition condition in the second layer thickness information. In addition, layer thickness information of a side corrected in accordance with the other layer thickness information out of the first layer thickness information and the second layer thickness information may be selectable. In this case, for example, the control unit 70 selects one of the first layer thickness information and the second layer thickness information as layer thickness information of a corrected side in accordance with the operation of an operation unit, and matches the selected layer thickness information with respect to an acquisition condition of the other layer thickness information.

Here, the correction data is, for example, data indicating the correction amount of a layer thickness. In this embodiment, correction data for matching the first layer thickness information and the second layer thickness information to each other is stored in the memory 72 in advance. For example, the correction amount in the correction data may be determined in advance as follows.

For example, a ratio (or a difference) of a layer thickness for each layer (or for each depth) in the first layer thickness information to that in the second layer thickness information, which is a ratio (or difference) not associated with changes in a subject eye over time, may be calculated in advance by acquiring OCT data regarding a layer-shaped object of which the interlayer distance is already known by each of the imaging apparatus 200 and the imaging apparatus 300 and comparing pieces of layer thickness information obtained from the respective pieces of OCT data with each other. The correction amount based on the ratio (or the difference) of the layer thickness, which is obtained in advance, may be specified in the correction data. Incidentally, the term "depth" means a depth defined in the OCT data and depends on a difference in an optical path between the measurement light and the reference light.

For example, in the above embodiment, the first layer thickness information and the second layer thickness information are matched to each other by correcting the layer thickness at the part of the retina inner layer and the layer thickness at the part of the retina outer layer (and deeper side thereof) by the difference amounts of correction. However, in the matching process, the layer structure (or depth structure) of the retina may be further segmentalized and the layer thickness may be corrected by the different amounts of correction for each segmentalized layer structure (or segmentalized depth structure).

In the embodiment, the correction data (mainly, correction amount of layer thickness information) is obtained by measuring a sample whose layer-to-layer distance is known. However, it is not limited to this way. For example, if the sample has a known thickness, it does not necessarily have to have a layer structure. In this case, the sample is disposed at each depth defined in the OCT data, and the layer thickness of the sample is measure by each of SD-OCT and SS-OCT. As a result, the measurement value of the thickness of the sample by each of SD-OCT and SS-OCT can be obtained for each depth where the sample is disposed.

The correction amount at a certain depth can be obtained based on the ratio of the measurement value of the thickness of the sample disposed at the certain depth for SD-OCT to the measurement value of the thickness of the sample disposed at the certain depth for the SS-OCT, or based on the difference between the measurement value of the thickness of the sample disposed at the certain depth for SD-OCT and the measurement value of the thickness of the sample disposed at the certain depth for the SS-OCT.

For example, in the above-described embodiment, a difference in at least any one of an imaging angle of view and a dimension per one pixel may be present as a difference in specifications between OCT data obtained by the imaging apparatus 200 and OCT data obtained by the imaging apparatus 300 (an example of a difference in acquisition condition). In this case, the control unit 70 may match the first layer thickness information and the second layer thickness information to each other in consideration of a difference in at least any one of an imaging angle of view and a dimension per one pixel. In this case, for example, correction data having a scale stored in the memory 72 in advance (for example, data for correcting a scale in the first layer thickness information and the second layer thickness information) may be acquired by the control unit 70 based on acquisition condition data associated with each of the first layer thickness information and the second layer thickness information. The control unit 70 may correct the scale of at least one of the first layer thickness information and the second layer thickness information based on the correction data during the matching process.

In addition, in the above-described embodiment, a description has been given of a case where the first layer thickness information and the second layer thickness information are matched to each other using correction data stored in the memory 72 in advance. However, the correction data used in a matching process does not necessarily have to be stored in the memory 72 in advance. For example, a correction expression in which the correction amount of a layer thickness for each layer is given as a function of an acquisition condition may be stored in the memory 72 or the like in advance, and thus the control unit 70 may calculate the correction amount from the correction expression in accordance with pieces of acquisition condition data of pieces of layer thickness information matched to each other every time a matching process is performed. The pieces of layer thickness information may be matched to each other based on the calculated correction amount.

In addition, in a matching process performed by the control unit 70 of the above-described embodiment, for example, each of the pieces of layer thickness information (at least any one of the first layer thickness information and the second layer thickness information) may be corrected with respect to the depth direction so as to obtain matching to layer thickness information of a normal eye (hereinafter, referred to as normal eye layer thickness information) which is stored in a normal eye database. The normal eye layer thickness information stored in the normal eye database may be results obtained by acquiring pieces of OCT data of a plurality of eyes under a certain acquisition condition (for example, by OCT data of a certain specification) and performing a predetermined statistic process on plural pieces of layer thickness information which are obtained from the respective pieces of OCT data. Accordingly, for example, layer thickness information regarding a normal eye in the normal eye database (referred to as normal eye layer thickness information) is data generated based on OCT data acquired under a first acquisition condition, while layer thickness information regarding a subject eye which is compared with the normal eye layer thickness information may be data generated based on OCT data acquired under a second acquisition condition (different from the first acquisition condition). As a specific example, a case is considered in which normal eye layer thickness information based on OCT data of a normal eye which is acquired by SD-OCT is stored in the normal eye database, and layer thickness information based on OCT data of a subject eye which is acquired by SS-OCT is compared with the normal eye layer thickness information.

On the other hand, layer thickness information (at least one of the first layer thickness information and the second layer thickness information) of a subject eye which is acquired by this apparatus 1 is corrected so as to achieve matching to normal eye layer thickness information, and thus it is possible to satisfactorily perform comparison between the layer thickness information regarding the subject eye and the normal eye layer thickness information. In addition, the control unit 70 may perform a process of comparing results of a matching process (the first layer thickness information and the second layer thickness information after the matching) with the normal eye layer thickness information, and may output results of the comparison. For example, the results of the comparison may be output as a comparison map and a deviation map which are described in the above-described embodiment. As a result, it is possible to compare layer thickness information regarding a subject eye with layer thickness information of a normal eye with a high level of accuracy in follow-up.

Meanwhile, in a case where the normal eye layer thickness information under the first acquisition condition and the layer thickness information regarding the subject eye under the second acquisition condition are matched to each other, at least one of the normal eye layer thickness information and the layer thickness information regarding the subject eye may be corrected with respect to the depth direction to thereby obtain matching results, and this disclosure is not limited to a case where only the layer thickness information regarding the subject eye is corrected as in the above-described modified example.

In this case, acquisition condition data of OCT data which is the base of a normal eye database may be stored in the memory 72 in advance together with the normal eye database. At least one of layer thickness information regarding a subject eye and layer thickness information of a normal eye database may be corrected based on acquisition condition data for layer thickness information of the normal eye database and acquisition condition data for the layer thickness information regarding the subject eye to thereby match the pieces of layer thickness information to each other.

In addition, in the above-described embodiment, as a specific example, a description has been given of a case where pieces of layer thickness information obtained by a plural types of OCT devices (in more detail, SD-OCT and SS-OCT) which differ in an imaging method are matched to each other. However, the technique of this disclosure may be applied to matching of pieces of layer thickness information obtained by devices which are OCT devices using the same type of imaging method and which differ in specifications of an optical system of an apparatus. For example, matching of pieces of layer thickness information obtained by a plurality of SD-OCT that differ in specifications of an optical system may be performed by the technique of this disclosure. In the case of SD-OCT, a typical example of "different specifications of optical systems" includes a case where at least one of wavelength regions of measurement light beams and spectrometers in two types of SD-OCT are different from each other.

In addition, in the above-described embodiment, a description has been given of a case where pieces of layer thickness information obtained from plural pieces of OCT data are matched to each other in consideration of a difference in specifications (an example of a difference in acquisition condition) between OCT devices that acquire pieces of OCT data. However, the difference in acquisition condition which is considered in matching the pieces of layer thickness information is not limited to a difference in specifications between the OCT devices. For example, the difference in acquisition condition may be a difference in condition regarding a parameter affecting a signal strength index (SSI) of OCT data. Meanwhile, examples of the parameter affecting an SSI of OCT data include the amount of measurement light emitted to a subject eye, a gain in a detector, and the like.

In addition, an alignment state during the acquisition of OCT data may be used as an acquisition condition of the OCT data in matching pieces of layer thickness information to each other. Examples of data for specifying the acquisition condition include pieces of front image data of the anterior ocular segment or the fundus which are acquired by the imaging apparatuses 200 and 300, results of detection of an alignment index, and the like together with OCT data.

In addition, in the above-described embodiment, a description has been given of a case where layer thickness information is generated from pieces of OCT data by the control unit 70 of this apparatus 1, but is not limited thereto. For example, layer thickness information based on each of the pieces of OCT data may be generated in each of the imaging apparatuses 200 and 300. A configuration may also be adopted in which the control unit 70 of this apparatus 1 acquires layer thickness information (that is, the first layer thickness information and the second layer thickness information) based on the pieces of OCT data by each of the pieces of layer thickness information being transmitted to this apparatus 1 through a network.

Meanwhile, this disclosure is not limited to the apparatus described in the above-described embodiment. For example, ophthalmologic image processing software (program) for performing the function of the above-described embodiment is supplied to a system or an apparatus through a network or various storage mediums. A computer (for example, a CPU or the like) of a system or an apparatus can also read out and execute a program.

What is claimed is:

1. An ophthalmologic information processing apparatus for performing follow-up of a subject eye based on plural pieces of optical coherence tomography, hereafter OCT, data obtained at different dates, the ophthalmologic information processing apparatus comprising:
   a processor; and
   memory storing computer readable instructions, when executed by the processor, causing the ophthalmologic information processing apparatus to execute:
   a first acquisition process of acquiring plural pieces of layer thickness information regarding a fundus, the plural pieces of layer thickness information being a processing result of the plural pieces of OCT data of the subject eye;
   a matching process of matching the pieces of layer thickness information based on the plural pieces of OCT data to each other in consideration of a difference in acquisition condition among the pieces of OCT data;
   a display control process of displaying results of the matching of the pieces of layer thickness information, which is performed by the matching process, on a monitor;
   wherein the plural pieces of OCT data includes first OCT data acquired by spectral domain OCT, hereafter SD-OCT, and second OCT data acquired by swept source OCT, hereafter SS-OCT;
   wherein the plural pieces of layer thickness information include first layer thickness information based on the first OCT data and second layer thickness information based on the second OCT data;
   wherein the matching process matches the first layer thickness information and the second layer thickness information to each other in consideration of a difference in sensitivity of an OCT signal with respect to a depth direction between the SD-OCT and the SS-OCT; and
   wherein the matching process corrects thickness with respect to one of the first layer thickness information and the second layer thickness information.

2. The ophthalmologic information processing apparatus according to claim 1, wherein
   the first acquisition process acquires layer thickness information regarding each layer of the fundus, and
   the matching process individually match at least layer thickness information regarding an inner layer of a retina and layer thickness information regarding an outer layer of the retina.

3. The ophthalmologic information processing apparatus according to claim 1, wherein the matching process matches the plural pieces of layer thickness information to each other for each layer constituting the fundus.

4. The ophthalmologic information processing apparatus according to claim 1, wherein the matching process matches the plural pieces of layer thickness information to each other for each depth of the fundus.

5. The ophthalmologic information processing apparatus according to claim 1,
   wherein the computer readable instructions causes the ophthalmologic information processing apparatus to execute:

a second acquisition process of acquiring normal eye layer thickness information which is layer thickness information regarding a normal eye from a normal eye database, and wherein the matching process corrects the plural pieces of layer thickness information regarding the subject eye with respect to a depth direction so as to achieve matching to the normal eye layer thickness information.

6. The ophthalmologic information processing apparatus according to claim 5, wherein the computer readable instructions causes the ophthalmologic information processing apparatus to execute:

comparison process of comparing the results of the matching of the pieces of layer thickness information, which is performed by the matching process, with the normal eye layer thickness information and outputting results of the comparison.

7. An ophthalmologic information processing apparatus for performing follow-up of a subject eye based on plural pieces of optical coherence tomography, hereafter OCT, data obtained at different dates, the ophthalmologic information processing apparatus comprising:

a processor; and memory storing computer readable instructions, when executed by the processor, causing the ophthalmologic information processing apparatus to execute:

a first acquisition process of acquiring plural pieces of layer thickness information regarding a fundus, the plural pieces of layer thickness information being a processing result of the plural pieces of OCT data of the subject eye;

a matching process of matching the pieces of layer thickness information based on the plural pieces of OCT data to each other in consideration of a difference in acquisition condition among the pieces of OCT data;

a display control process of displaying results of the matching of the pieces of layer thickness information, which is performed by the matching process, on a monitor;

wherein the matching process corrects thickness regarding one of the first layer thickness information and the second layer thickness information which is deeper in a depth direction than a depth determined in advance as a threshold value.

8. An ophthalmologic information processing apparatus for performing follow-up of a subject eye based on plural pieces of optical coherence tomography, hereafter OCT, data obtained at different dates, the ophthalmologic information processing apparatus comprising:

a processor; and memory storing computer readable instructions, when executed by the processor, causing the ophthalmologic information processing apparatus to execute:

a first acquisition process of acquiring plural pieces of layer thickness information regarding a fundus, the plural pieces of layer thickness information being a processing result of the plural pieces of OCT data of the subject eye;

a matching process of matching the pieces of layer thickness information based on the plural pieces of OCT data to each other in consideration of a difference in acquisition condition among the pieces of OCT data;

a display control process of displaying results of the matching of the pieces of layer thickness information, which is performed by the matching process, on a monitor; and wherein the matching process corrects the error in the layer thickness between the first layer thickness information and the second layer thickness information by correction amounts which differs for each layer constituting the fundus.

9. The ophthalmologic information processing apparatus according to claim 8, wherein the correction amount for any layer among the layers constituting the fundus is obtained based one of a ratio of the measurement value of the thickness obtained by SD-OCT to the measurement value of the thickness obtained by SS-OCT and a difference between the measurement value of the thickness obtained by SD-OCT and the measurement value of the thickness obtained by SS-OCT, and the ratio is obtained based on the measurement value obtained by arranging a sample having a known thickness at said any layer, measuring the thickness of the sample and obtaining the ratio or the difference of the measurement thickness of the sample with respect to the layers.

10. An ophthalmologic information processing apparatus for performing follow-up of a subject eye based on plural pieces of optical coherence tomography, hereafter OCT, data obtained at different dates, the ophthalmologic information processing apparatus comprising:

a processor; and memory storing computer readable instructions, when executed by the processor, causing the ophthalmologic information processing apparatus to execute:

a first acquisition process of acquiring plural pieces of layer thickness information regarding a fundus, the plural pieces of layer thickness information being a processing result of the plural pieces of OCT data of the subject eye;

a matching process of matching the pieces of layer thickness information based on the plural pieces of OCT data to each other in consideration of a difference in acquisition condition among the pieces of OCT data;

a display control process of displaying results of the matching of the pieces of layer thickness information, which is performed by the matching process, on a monitor; and wherein the matching process corrects the error in the layer thickness between the first layer thickness information and the second layer thickness information by correction amounts which differs for each depth of the fundus.

11. The ophthalmologic information processing apparatus according to claim 10, wherein the correction amount for any depth of the fundus is obtained based one of a ratio of the measurement value of the thickness obtained by SD-OCT to the measurement value of the thickness obtained by SS-OCT and a difference between the measurement value of the thickness obtained by SD-OCT and the measurement value of the thickness obtained by SS-OCT, and the ratio is obtained based on the measurement value obtained by arranging a sample having a known thickness at said any depth, measuring the thickness of the sample and obtaining the ratio or difference of the measurement thickness of the sample with respect to the depth.

12. An ophthalmologic information processing method for performing follow-up of a subject eye based on plural pieces of optical coherence tomography, hereafter OCT, data obtained at different dates and times, the ophthalmologic information processing method comprising:
- a first acquisition process of acquiring plural pieces of layer thickness information regarding a fundus, the plural pieces of layer thickness information being a processing result of the plural pieces of OCT data of the subject eye;
- a matching process of matching the pieces of layer thickness information based on the plural pieces of OCT data to each other in consideration of a difference in acquisition condition among the pieces of OCT data; and
- a display control process of displaying results of the matching of the pieces of layer thickness information, which is performed by the matching process, on a monitor;
- wherein the plural pieces of OCT data includes first OCT data acquired by spectral domain OCT, hereafter SD-OCT, and second OCT data acquired by swept source OCT, hereafter SS-OCT;
- wherein the plural pieces of layer thickness information include first layer thickness information based on the first OCT data and second layer thickness information based on the second OCT data;
- wherein the matching process matches the first layer thickness information and the second layer thickness information to each other in consideration of a difference in sensitivity of an OCT signal with respect to a depth direction between the SD-OCT and the SS-OCT; and
- wherein the matching process corrects thickness with respect to one of the first layer thickness information and the second layer thickness information.

* * * * *